United States Patent [19]

Nelson

[11] 3,998,941
[45] Dec. 21, 1976

[54] PREPARATION OF ALKALI METAL HYDRIDES

[75] Inventor: Gunner E. Nelson, Baton Rouge, La.

[73] Assignee: Ethyl Corporation, Richmond, Va.

[22] Filed: Oct. 4, 1974

[21] Appl. No.: 512,120

[52] U.S. Cl. .............................................. 423/646
[51] Int. Cl.² ......................................... C01B 1/00
[58] Field of Search ................ 260/448 A; 423/646

[56] References Cited
UNITED STATES PATENTS

| | | | |
|---|---|---|---|
| 2,786,860 | 3/1957 | Ziegler et al. | 260/448 A |
| 2,915,542 | 12/1959 | Robinson et al. | 260/448 A |
| 3,098,706 | 7/1963 | Blitzer et al. | 260/448 A X |
| 3,143,542 | 8/1964 | Ziegler et al. | 260/448 A X |
| 3,686,248 | 8/1972 | Nelson | 260/448 A |

FOREIGN PATENTS OR APPLICATIONS 1,116,664   11/1961   Germany

OTHER PUBLICATIONS

Ashby et al., Inorganic Chemistry, V2, pp. 499–504 (1963).
Ashby et al., Inorganic Chemistry, V5, pp. 1615–1617 (1966).

Primary Examiner—Helen M. S. Sneed
Attorney, Agent, or Firm—Donald L. Johnson; John F. Sieberth; Shelton B. McAnelly

[57] ABSTRACT

This invention relates to the preparation of alkali metal hydrides and of alkali metal aluminum dihydrocarbon dihydrides and in particular to such compounds of sodium, potassium or lithium having in the case of the dihydrocarbon compounds hydrocarbon radicals containing from 2 to about 30 carbon atoms per radical. Such dihydrocarbon materials, as typified by sodium aluminum diethyl dihydride, and by the potassium or lithium counterparts, either singly or in mixtures with respect to alkali metals and hydrocarbon groups, are soluble and useful in inert aromatic hydrocarbon solutions and have excellent mild reducing properties for various functional groups such as carbonyl groups in various organic compounds. The alkali metal hydrides are useful in many known ways such as in condensation and alkylation reactions and as chemical intermediates such as in the preparation of the alkali metal aluminum dihydrocarbon dihydrides.

25 Claims, 2 Drawing Figures

PREPARATION OF ALKALI METAL HYDRIDES

DESCRIPTION OF THE PRIOR ART

Alkali Metal Hydride Processes

One known method of preparing alkali metal hydrides utilizes the reaction of alkali metal and hydrogen in the presence of alkali metal hydride. In such operation, the alkali metal hydride may expedite the reaction but the effect is not truly catalytic and more a matter of surface effect since other particulate solid dispersants such as sand, clay, or the like, are about as effective. Even in such systems, it is considered desirable to operate with close control of the balance between alkali metal and hydrogen fed to prevent the existence of a liquid phase which may stop the reaction and cause rapid build-up of scale. Another factor involved in the use of alkali metal hydride as a dispersant is the problem of residual moisture in the reactants fed and in the reactor in start-up and the need to avoid water presence because of the violent reaction with moisture characteristic of alkali metals and their hydrides.

In another method, alkali metal hydrides are prepared by reacting alkali metal and hydrogen in a heavy hydrocarbon oil diluent. Such processing usually provides a slurry type product that is no more than about 50 percent alkali metal hydride and it is difficult to remove the heavy hydrocarbon by vaporization or filtration which generally dictates the use of expensive solvent or extraction removal procedures or the shipment and use of the alkali metal hydride in the form of a dispersion in oil. Even these procedures have the disadvantage that the mineral oil diluent and extractant used must be water free.

Alkali Metal Aluminum Dihydrocarbon Dihydride Processes

Previously known processes for the preparation of alkali metal aluminum dihydrocarbon dihydrides have suffered from several disadvantages. German Pat. No. 918,928 describes the preparation of sodium or lithium aluminum dialkyl dihydrides by reacting dialkyl aluminum hydrides or dialkyl aluminum halides with sodium hydride. These reactions preferably are conducted with oil-free alkali metal hydride to avoid the need for subsequent removal of the oil present with oil-dispersion sodium hydride.

The dialkyl aluminum halide reaction further suffers from the disadvantage that it requires the preparation of the halide material and that in the process some of the alkali metal value is converted to an alkali metal halide salt of low value.

Another process for producing alkali metal aluminum dihydrocarbon dihydrides is shown in German Pat. No. 1,116,664 wherein trialkyl aluminum is reacted with alkali metal and hydrogen. This process suffers from the disadvantage that one of the three alkyl groups on the starting trialkyl aluminum is lost by conversion thereof to hydrocarbon.

Another process for producing alkali metal aluminum dihydrocarbon dihydrides is described in U.S. Pat. No. 3,686,248. Although this is an excellent process for producing the desired product in high yield, further improvement is desirable since at times there may be a tendency toward the deposition of aluminum on reactor surfaces.

SUMMARY OF THE INVENTION

The present process avoids much of the prior art difficulty associated with the preparation of alkali metal hydrides as well as with the preparation of alkali metal aluminum dihydrocarbon dihydrides. The present process provides a catalyzed process for producing alkali metal hydride at a high rate, in a high level of safety, and without contamination by heavy oil or other materials that are not desired in alkali metal aluminum dihydrocarbon dihydrides or other materials produced from the alkali metal hydrides. The process of the present invention utilizes the alkali metal hydride to produce alkali metal aluminum dihydrocarbon dihydride while avoiding the need for an alkali metal hydrocarbon halide raw material.

An important aspect of the present process is the catalyzed production and use of an alkali metal hydride to produce alkali metal aluminum dihydrocarbon dihydrides that does not require difficult purification to remove impurity materials undesired in alkali metal aluminum dihydrocarbon dihydrides produced therefrom.

In the present process, alkali metal hydride is produced by reacting alkali metal and hydrogen in the presence of a solution of alkali metal aluminum dihydrocarbon dihydride in inert aromatic hydrocarbon.

The alkali metal hydride thus obtained is highly desirable for the production of alkali metal aluminum dihydrocarbon dihydride by additional process steps wherein trihydrocarbon aluminum compound, especially a trialkyl aluminum compound such as triethyl aluminum is added and the resulting mixture is reacted with aluminum and hydrogen under conditions which form the desired sodium aluminum dihydrocarbon dihydride.

DESCRIPTION OF THE PREFERRED EMBODIMENTS

Figure 1:
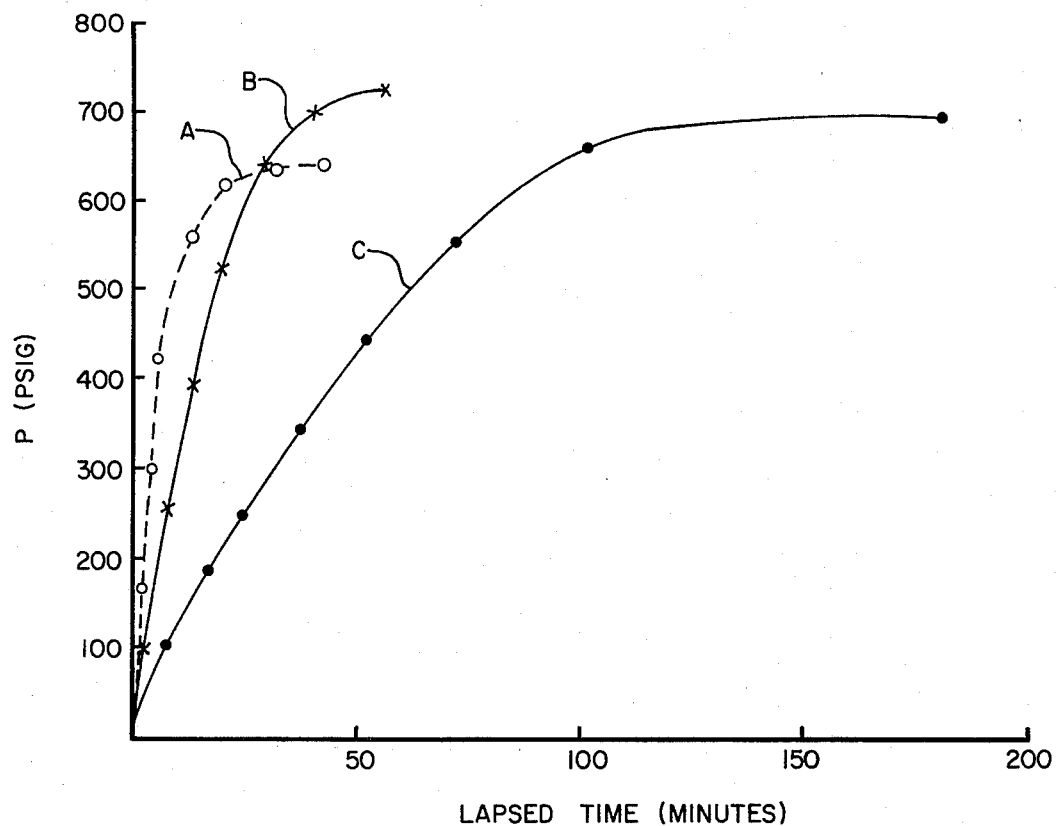
FIG. 1 of the drawings shows a group of three curves of pressure versus reaction time for the sodium hydride formation step of Examples I, II, III and IV.
Figure 2:
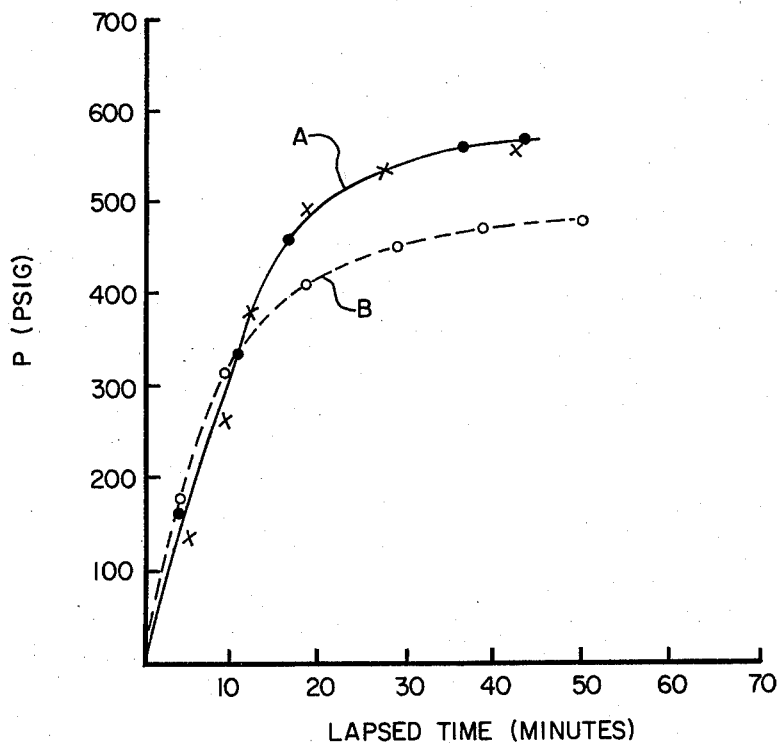
FIG. 2 of the drawings shows a group of two curves of pressure versus reaction time for the sodium hydride formation step of Examples V, VI and VII.

The present process provides a way to avoid the foregoing and other problems of the prior art and at the same time provides a catalytic effect to enhance the rate of reaction of alkali metal and hydrogen in the formation of alkali metal hydride.

The present process is of particular value in the preparation of alkali metal hydrides to be used as intermediates for the preparation of other materials such as alkali metal aluminum dihydrocarbon dihydrides, typically sodium aluminum diethyl dihydride, from trihydrocarbon aluminums such as triethyl aluminum. Sodium aluminum diethyl dihydride typically is an excellent reducing agent for carbonyl and nitrile groups. In addition to the preparation of alkali metal hydrides, the present invention provides a process for the production of alkali metal aluminum dihydrocarbon dihydrides utilizing a catalyzed reaction of alkali metal and hydrogen. As will be brought out in greater detail hereinafter, the present invention avoids certain problems previously encountered in the preparation of alkali metal aluminum dihydrocarbon dihydrides.

An important discovery is the catalytic effect of alkali metal aluminum dihydrocarbon dihydride in the preparation of alkali metal hydrides. Preferably the amount of alkali metal aluminum dihydrocarbon dihydride is a catalytic amount of at least about 0.001 percent by weight based on the alkali metal reactant fed to the process. The use of alkali metal aluminum dihydrocarbon dihydride as a catalyst is an important contribution because of its solubility properties. Unlike the alkali metals and their hydrides, alkali metal aluminum dihydrocarbon dihydrides are soluble to a substantial extent in certain aromatic hydrocarbons as disclosed in U.S. Pat. Nos. 3,686,248 and 3,696,047. This solubility characteristic permits the use of a liquid catalytic system to improve contact and reaction between alkali metal and the hydrogen. The solvent, or diluent, is desirably inert which means that it does not undergo reaction or degradation in an undesired way in the reaction or in the use of the reaction product. The reaction to form alkali metal hydride is conducted at a temperature of from about 100° to about 325° C and a pressure of from about 50 to about 5000 psig for a period of time of from about 0.01 to about 12 hours.

Preferably the alkali metal used to produce the alkali metal component of the alkali metal hydride is sodium, potassium or lithium, listing them in the order of preference; however, other alkali metals of Group I-A of the Periodic Table (Fisher Scientific Co. 1955) can be used. The alkali metal of the alkali metal aluminum dihydrocarbon dihydride used in the process is preferably the same as the alkali metal reacted with hydrogen to produce the alkali metal hydride. This preference is directed toward securing a greater uniformity of product. In other instances, the alkali metal of the alkali metal aluminum dihydrocarbon dihydride is different from alkali metal fed for the reaction with hydrogen. Thus, for example, one may use potassium or sodium aluminum diethyl dihydride as catalyst in the preparation of sodium hydride or potassium hydride, respectively.

The alkali metal aluminum dihydrocarbon dihydride used is preferably of the formula $MAlR_2H_2$ wherein M is alkali metal and R is similar or different alkyl group having from about 2 to about 30 carbon atoms per alkyl group. More preferably, R is similar or different alkyl group having from about 2 to about 6 carbon atoms per alkyl group. Preferably, the alkali metal aluminum dihydrocarbon dihydride is sodium aluminum diethyl dihydride or sodium aluminum diisobutyl hydride, especially the former.

Preferably the temperature of the process is from about 150° C to about 275° C, especially from about 175° C to about 225° C.

The amount of alkali metal aluminum dihydrocarbon dihydride catalyst used is not especially critical as long as at least a catalytic amount is present; however, preferably the amount is from about 0.1 percent to about 50 percent by weight based on the alkali metal fed to the process for the reaction with hydrogen, especially from about 1 percent to about 20 percent by weight, particularly from about 10 to about 15 percent by weight.

In a preferred aspect of the present process, the pressure is from about 500 to about 1250 pounds per square inch gage. Pressure is not a critical variable in this instance; however, a good rate of reaction is facilitated by using pressures of the order of 750 pounds per square inch gage and higher while on the other hand pressures in excess of 1250 pounds per square inch gage are unnecessary for a good rate and hence are usually preferably avoided to minimize construction expenses attendant to operation at higher pressures.

Solvents used in the present process are preferably inert aromatic hydrocarbon for the alkali metal aluminum dihydrocarbon dihydride catalyst used in the present process. In regard to the alkali metal and the alkali metal hydride, these solvents are obviously essentially only diluents; however, they do facilitate contact between the alkali metal and the catalyst. Preferred solvents are toluene, xylene and benzene since these are inert, are readily available at low cost and because the alkali metal aluminum dihydrocarbon dihydrides have excellent solubility therein. As a preferred aspect, the solvent is chosen so as to represent a preferred solvent for product alkali metal aluminum dihydrocarbon dihydride especially if the present alkali metal hydride process is used as a method of providing alkali metal hydride for use as a raw material in the preparation of the alkali metal aluminum dihydrocarbon dihydride. Since toluene, xylene and benzene are preferred solvents for the handling and use of alkali metal aluminum dihydrocarbon dihydrides, it is usually preferred to use one of these solvents in the alkali metal hydride production step and to carry the solvent through the succeeding step whereby the alkali metal aluminum dihydrocarbon dihydride is produced from the alkali metal hydride. Since the solvent is exposed to elevated temperatures in the process, it is preferred to utilize a solvent which has a high critical temperature to which end toluene is a preferred solvent.

In a preferred aspect of the present invention, the temperature is from about 150° C to about 275° C, the pressure is from about 500 to about 1250 pounds per square inch gage and the catalytic quantity of alkali metal aluminum dihydrocarbon dihydride is from about 10 to about 15 percent by weight based on the sodium fed to the process for reaction with hydrogen.

Due to the excellence of the preparation of alkali metal hydride by the present process and the form of the alkali metal hydride produced thereby, the present invention provides an excellent plural step process for the preparation of alkali metal aluminum dihydrocarbon dihydrides using directly the mixture of alkali metal hydride, alkali metal aluminum dihydrocarbon dihydride catalyst and solvent from the production of the alkali metal hydride in subsequent reaction with trialkyl aluminum, aluminum and hydrogen. Thus the present invention also is directed to a process for producing alkali metal aluminum dihydrocarbon dihydrides which comprises first reacting alkali metal and hydrogen in the presence of an inert aromatic hydrocarbon solvent for the alkali metal aluminum dihydrocarbon dihydride and a catalytic amount of at least about 0.001 percent by weight of alkali metal aluminum dihydrocarbon dihydride. The foregoing reaction is suitably performed under conditions suitable to form alkali metal hydride so that alkali metal hydride is produced. To the alkali metal hydride thus obtained and without need for removal of the solvent or the alkali metal aluminum dihydrocarbon dihydride, is then added trialkyl aluminum. The mixture thus obtained is then reacted with aluminum and hydrogen in the presence of said solvent under conditions suitable to form alkali metal aluminum dihydrocarbon dihydride thereby producing alkali metal aluminum dihydrocarbon dihydride. Thus one obtains a system containing alkali metal aluminum dihydrocarbon dihydride and inert aromatic hydrocarbon solvent wherein the amount of alkali metal aluminum dihydrocarbon dihydride is greater than the amount thereof used as catalyst at step 1.

In greater particularity, the present invention is directed to a process for producing alkali metal aluminum dihydrocarbon dihydrides which comprises reacting alkali metal and hydrogen in the presence of an inert aromatic hydrocarbon solvent for the alkali metal aluminum dihydrocarbon dihydride and a catalytic amount of at least about 0.001 percent by weight of alkali metal aluminum dihydrocarbon dihydride based on the alkali metal fed to the process. This reaction is suitably performed at a temperature of from about 100° to about 325° C, and a pressure of from about 50 to about 5000 psig for a period of time of from about 0.01 to about 12 hours, thereby producing alkali metal hydride. To the alkali metal hydride thus obtained and without need for removal of the solvent or the alkali metal aluminum dihydrocarbon dihydride is then added trihydrocarbon aluminum. The mixture thus obtained is then reacted with aluminum and hydrogen in the presence of said solvent at a temperature of from about 100° to about 325° C and a pressure of from about 50 to about 5000 psig for a period of time of from about 0.01 to about 12 hours, thereby producing alkali metal aluminum dihydrocarbon dihydride. Thus one obtains a system containing an aluminum dihydrocarbon dihydride and inert aromatic hydrocarbon solvent wherein the amount of alkali metal aluminum dihydrocarbon dihydride is greater than the amount thereof used as catalyst at step 1.

Preferably the hydrocarbon aluminum compound is a trialkyl aluminum having from about 2 to about 30 carbon atoms per alkyl group, especially one having from about 2 to about 6 carbon atoms per alkyl group, typically triethyl aluminum or tri-isobutyl aluminum.

Typically sodium, potassium or lithium is reacted ultimately to produce respectively sodium aluminum dihydrocarbon dihydride, potassium aluminum dihydrocarbon dihydride or lithium aluminum dihydrocarbon dihydride.

Preferably the pressure of the reactions with hydrogen is from about 100 to about 2000 pounds per square inch gage, especially from about 500 to about 1250 pounds per square inch gage.

Preferably the temperature of the reactions with hydrogen is from about 150° C to about 275° C, especially from about 175° C to about 225° C.

Preferably the temperature of the reaction of alkali metal and hydrogen is about 225° C, the temperature at step 2 where the trihydrocarbon aluminum is added is from about room temperature to about 225° C and the temperature of step 3 at the reaction of alkali metal hydride, trihydrocarbon aluminum, aluminum and hydrogen is about 175° C.

The amount of catalyst alkali metal aluminum dihydrocarbon dihydride to be used in the catalyzed reaction of alkali metal and hydrogen to produce alkali metal hydride is not critical. In general, at least a catalytic amount is used. The minimum practical catalytic amount added as well as the optimum amount is readily determined for specific cases by simple routine experimentation using the procedures described herein and used in the appended examples. In general, the minimum catalytic amount is about 0.001 percent by weight based upon the alkali metal fed for reaction with the hydrogen. On the other hand, since the present invention discloses the basic catalysis, the term "effective amount" includes any amount deliberately added or retained to achieve catalysis. Although there is no upper limit upon the amount of catalyst that can be used, generally there is no particular need to feed more catalyst than about 50 percent by weight based upon the alkali metal fed for the reaction and above this amount, reactor capacity is needlessly monopolized by catalyst. Of course, if one wishes to use more catalyst, the fundamental process is admirably suited to such in most instances since the catalyst is soluble in aromatic hydrocarbons such as toluene and others recited herein while the reactant sodium and product sodium hydride are virtually insoluble in such hydrocarbons. Thus simple decantation or filtration operations can readily separate the catalyst. Furthermore, since the catalyst is a material that is also an especially desirable product readily manufactured as disclosed herein from alkali metal hydride, the separation of the catalyst from the alkali metal hydride is frequently entirely unnecessary leaving the reactor monopolization factor as the principal reason for specifying an upper limit upon the amount of catalyst to use.

Since the alkali metals represents a small class of materials with mutually similar properties, the various alkali metals behave similarly as reactants to produce alkali metal hydride or as catalyst components in the alkali metal aluminum dihydrocarbon dihydrides. Thus the choice of alkali metal for either is usually a matter of economics or of the purpose for which the product is to be used. Particularly is this true of the reduction use of alkali metal aluminum dihydrocarbon dihydrides wherein the important aspect is the reactivity of the Al—H bonds, and whose alkali metal and hydrocarbon constituents go mainly to establishing physical properties such as solubility, melting point, molecular weight, etc. Thus mixtures of two or more alkali metals may be used as reactants or as catalyst components and the alkali metal reactants are suitably the same as the catalyst components or different therefrom.

The hydrocarbon radicals of the alkali metal aluminum dihydrocarbon dihydrides used as catalysts for the preparation of alkali metal hydride or of the product of the utilization of the alkali metal hydride to produce alkali metal aluminum dihydrocarbon dihydride suitably are alkyl groups having from about 2 to about 30 carbon atoms per radical, although they can be olefinic and can contain innocuous substitution, generally they are primarily of a "carrier" nature so that the expense, availability and reactivity are the principal factors which suggest or control which radicals are preferred. Thus preferred hydrocarbon radicals are alkyl groups, especially those having from two to about six carbon atoms per group. Typical preferred radicals are ethyl, propyl, isopropyl, n-butyl, isobutyl, n-pentyl, n-hexyl and the like. A preferred radical is ethyl since this is readily obtained by using low cost readily available, excellently reactive triethyl aluminum as a reactant in the process of the present invention and lower molecular weight hydrides (i.e., those with the smaller hydrocarbon radicals) have greater effectiveness per pound as reducing agents.

The solvents suitable for the present invention are quite limited. In the first place it is obvious that any solvent or diluent used must be inert, that is, not adversely reactive with any of the materials present or itself adversely degraded under the conditions used.

Secondly, the solvent or diluent is desired to be a solvent for the catalyst used in the preparation of the alkali metal hydride or at least for the minimum effective amount of catalyst. The solvent or diluent is suitably merely a diluent in regard to the alkali metal reactant or alkali metal hydride product. In general, suitable solvents or diluents are readily identified from solubility data and reactivity properties so that candidates are readily revealed by routine experimentation following the appended examples.

Suitable solvents or diluents are inert aromatic hydrocarbon solvents including toluene, benzene, xylene, ethylbenzene.

As noted hereinbefore, the amount of the solvent or diluent used is not critical. In general, one desires to use enough solvent to solubilize at least the minimum effective amount of catalyst. Usually, it is preferred to use enough solvent to maintain a fluid system which can be agitated effectively during the respective reactions by conventional propeller or turbine stirrers for both the production of alkali metal hydride and for the production of the alkali metal aluminum dihydrocarbon dihydride. Where the production of alkali metal hydride is for the purpose of converting it to alkali metal aluminum dihydrocarbon dihydride, it is usually preferred to feed at the first step of production of the alkali metal hydride an amount of from about one-quarter to about 100 percent of the solvent required to solubilize all of the final product alkali metal aluminum dihydrocarbon dihydride. In this range, but especially with about one-half of the required solvent for the product alkali metal aluminum dihydrocarbon dihydride final product, one obtains a good compromise between fluidity of the reaction masses and avoidance of excessive monopolization of reactor volume by solvent. Where less than the total solvent required to solubilize the product alkali metal aluminum dihydrocarbon dihydride is fed during the reactions, it is usually desired to add the balance of the needed solvent to the reaction mass after the reaction to facilitate product removal from the reactor; however, such may not be desirable where a heel of the product alkali metal aluminum dihydrocarbon dihydride is retained in the reactor as catalyst for a subsequent run.

The preferred alkali metal aluminum dihydrocarbon dihydride compounds are soluble to at most only about 30 percent by weight in the solvents. Normally this is not of any particular problem except where the production of the most concentrated product alkali metal aluminum dihydrocarbon dihydride is desired, for example, to minimize shipping costs. In such instances, the solubility of alkali metal aluminum dihydrocarbon dihydride can be enhanced considerably through the use of suitable innocuous Lewis bases as co-solvent as described in U.S. Pat. No. 3,696,047, the disclosure of which, like the disclosure of U.S. Pat. No. 3,686,248, is herewith incorporated herein by reference. Thus, for example, as shown by Example V, one can add such Lewis bases as tetrahydrofuran after the final step reaction. In general, it is preferred to avoid the presence of the Lewis bases during the hydrogenation reactions so that where a heel of the alkali metal aluminum dihydrocarbon dihydride is to be retained in the reactor or a portion withdrawn and returned as catalyst, it is preferred to add the Lewis base to the product system after provision has been made for the retention of catalyst material.

The reaction to produce alkali metal aluminum dihydrocarbon dihydride from alkali metal hydride requires the feed not only of trihydrocarbyl aluminum and hydrogen but also the feed of aluminum, preferably of a reactive or activated type, preferably in the form of powder. Preferred aluminum powder contains an alloying agent such as titanium or zirconium to enhance the reactivity. It is believed that the reactions proceed as indicated hereinafter:

3 NaH + 2 R₃Al → 2 NaAlR₃H + NaH

2 NaAlR₃H + NaH + Al +1-½ H₂ → 3 NaAlR₂H₂

The addition of the extra aluminum to the NaH or to the combined NaH and R₃Al system is not particularly convenient. Thus it is usually preferred to add the required amount of aluminum to the reactor prior to the reaction which produces the alkali metal hydride and to carry it on through to the point where it reacts. The present examples I and II appended indicate that the presence of the aluminum does not adversely affect the production of the alkali metal hydride. The amount of aluminum fed is usually at least the amount required for conversion of the alkali metal hydride and trihydrocarbon aluminum to alkali metal aluminum dihydrocarbon dihydride at the last stage. The feed of an excess of aluminum, e.g. 1–20 percent, is usually desirable to insure complete reaction at a rapid rate. The feed of an excess of aluminum normally presents no problem since the excess left unreacted is readily retained in the reactor or separated and returned to it for use in a subsequent batch.

The physical conditions used for the reaction are not critical and have been disclosed herein to an extent more than ample to permit optimization in any respect by routine experimentation by one of ordinary skill in the art. The present examples illustrate the effect of various factors, seeking substantially complete reaction of the limiting reactant or reactants to the product of each respective stage.

Thus the aluminum and hydrogen are usually fed in excess above the stoichiometric amount required for the various reactions, the limiting reactant being the alkali metal in the case of the production of alkali metal hydride and either the alkali metal hydride or the trihydrocarbon aluminum in the case of the preparation of alkali metal aluminum dihydrocarbon dihydride from the alkali metal hydride. Normally, however, one prefers to use stoichiometric proportions of three mols of alkali metal hydride and two mols of trihydrocarbon aluminum in the conversion of the alkali metal hydride to alkali metal aluminum dihydrocarbon dihydride.

For the examples, the reactor and all reactants fed are preferably placed in an anhydrous condition; however, residual moisture is readily removed where necessary by a preliminary contacting of the materials, for example, the toluene with alkali metal aluminum dihydrocarbon dihydride such as sodium aluminum diethyl dihydride or feeding the alkali metal last or bubbling the hydrogen through alkali metal aluminum dihydrocarbon dihydride. This material reacts readily but gently with water avoiding the violent reactions experienced where the water is contacted first with trihydrocarbon aluminum, alkali metal or alkali metal hydride.

From the foregoing and from the appended examples and claims, it is apparent to those skilled in the art that numerous arrangements can be made of the teachings, features and aspects of the present invention and that the invention is not to be limited except in accordance with the appended claims.

EXAMPLES I–IV

A 2-liter stainless steel Parr reactor equipped with external electric heater, internal cooling coils, baffles and twin-turbine air driven stirrer, thermometer, pressure gage and hydrogen feed system was used for Examples I–IV.

EXAMPLE I

The 2-liter reactor was charged with 800 ml of toluene, 81.5 grams of sodium and 8.15 grams of sodium aluminum diethyl dihydride, the latter in a 25 wt. percent solution in toluene. The system was purged with hydrogen and approximately 100 psig hydrogen pressure allowed to remain in the reactor as heating was begun. The stirrer was turned on when the temperature reached 125° C. (The melting point of sodium is 97.5° C.) When the temperature reached 220° C, the reactor was pressurized with hydrogen to about 1000 psig and the hydrogen supply valve closed. After two minutes, the pressure had dropped 160 psig and the reactor was again pressurized with hydrogen to about 1000 psig and the hydrogen supply again closed. After five minutes from the start of operation at 1000 psig, the pressure gage was again read. This time the pressure had dropped 140 psig. Again the reactor was quickly pressured to about 1000 psig following which a drop of 120 psig was observed at the 8 minute point. The procedure was continued with measurement and rapid repressurization to about 1000 psig at the 13, 20, 23, 28 and 41 minute points. The pressure drop results are tabulated hereinafter in the column, the consecutive pressure drops being added together in sequence to provide the Σ pressure drop figures which are those used in plotting Curve A of FIG. 1. Throughout the procedure the reactor temperature was held at about 220° C. The foregoing procedure is a simple way to determine reaction rate without requiring exact flow rate measurement for the pressurized hydrogen.

| Time (Minutes) | Pressure (psig) Δ | Pressure (psig) Σ |
|---|---|---|
| 0 | — | — |
| 2 | 160 | 160 |
| 5 | 140 | 300 |
| 8 | 120 | 420 |
| 13 | 130 | 550 |
| 20 | 80 | 630 |
| 23 | 20 | 650 |
| 28 | 5 | 655 |
| 41 | 5 | 660 |

After the reaction, the vessel was cooled, the hydrogen pressure released and the dispersion of NaH in toluene discharged into a receiver. The dispersion was filtered to separate the sodium hydride from the toluene solution of sodium aluminum diethyl dihydride catalyst. The solid remaining was analyzed and shown to be NaH of purity higher than 95 percent.

EXAMPLE II

Example I was repeated at 225° C using 100 grams of sodium, 50 grams of powdered aluminum, and 5 grams of sodium aluminum diethyl dihydride.

| Time (Minutes) | Pressure (psig) Δ | Pressure (psig) Σ |
|---|---|---|
| 0 | — | — |
| 3 | 100 | 100 |
| 9 | 150 | 250 |
| 15 | 140 | 390 |
| 21 | 130 | 520 |
| 30 | 120 | 640 |
| 41 | 60 | 700 |
| 57 | 20 | 720 |

The reaction rates of Examples I and II are comparable showing that the presence of the aluminum in Example II does not significantly affect reaction rate.

EXAMPLE III

Example I was repeated at 270° C but using 100 grams of sodium, and 50 grams of aluminum powder.

| Time (Minutes) | Pressure (psig) Δ | Pressure (psig) Σ |
|---|---|---|
| 0 | — | — |
| 5 | 140 | 140 |
| 10 | 100 | 240 |
| 21 | 110 | 350 |
| 35 | 70 | 420 |
| 65 | 90 | 510 |

EXAMPLE IV

Example I was repeated at 225° C with 490 ml toluene and 106.5 grams of sodium.

| Time (Minutes) | Pressure (psig) Δ | Pressure (psig) Σ |
|---|---|---|
| 0 | — | — |
| 7 | 105 | 105 |
| 18 | 80 | 185 |
| 25 | 60 | 245 |
| 37 | 100 | 345 |
| 52 | 100 | 445 |
| 73 | 105 | 550 |
| 102 | 110 | 660 |
| 182 | 30 | 690 |

The preceding examples show a significantly higher reaction rate when the reaction is conducted in the presence of catalyst as specified and indicate that the presence of the aluminum powder does not significantly affect the reaction rate. Thus where the sodium hydride is subsequently reacted with triethyl aluminum and hydrogen to produce sodium aluminum diethyl dihydride, the aluminum powder needed for the latter reaction is suitably and conveniently added to the reactor prior to the formation of the sodium hydride.

EXAMPLES V–VII

These examples were conducted in a 5-gallon stainless steel pressure vessel, jacketed for heating externally. The vessel was equipped with pressure gage, thermometer, a hydrogen feed system, internal cooling coil for temperature maintenance and rapid cooling after the reaction. The reactor was baffled and equipped with an electrically driven twin turbine stirrer. Pressuring with hydrogen was periodic to 1000 psig as in Examples I–IV.

EXAMPLE V

The 5-gallon reactor was charged with 5800 grams toluene, 270 grams aluminum powder, 644 grams sodium, and 340 grams of a 25 percent solution of sodium aluminum diethyl dihydride in toluene. (85 grams of contained $NaAlEt_2H_2$, 13.2 percent on the sodium fed for the reaction with hydrogen). The reactor was purged with hydrogen, leaving 100 psig residual hydrogen pressure. The heater was turned on and the stirrer started when the temperature reached 150° C. Reactor heating was continued until a temperature of 220° C was reached, which temperature was subsequently maintained during the course of the reaction. Hydrogen was then fed for a 43 minute total reaction time.

| Time (Minutes) | Pressure (psig) Δ | Pressure (psig) Σ |
|---|---|---|
| 0 | — | — |
| 4 | 160 | 160 |
| 10 | 170 | 330 |
| 16 | 130 | 460 |
| 27 | 70 | 530 |
| 36 | 30 | 560 |
| 43 | 10 | 570 |

The reactor was then cooled to 50° C, hydrogen pressure vented off and 2240 grams of liquid triethyl aluminum pressured into the reactor from a cylinder of triethyl aluminum.

The reactor was then heated to 170° C under hydrogen and then hydrogen was fed for a reaction time of 52 minutes at 170° C. Pressuring with hydrogen was periodic to 1000 psig as in the preceding sodium hydride preparation.

| Time (Minutes) | Pressure (psig) Δ | Pressure (psig) Σ |
|---|---|---|
| 0 | — | — |
| 1 | 160 | 160 |
| 4 | 140 | 300 |
| 13 | 140 | 440 |
| 22 | 90 | 530 |
| 33 | 90 | 620 |
| 44 | 100 | 720 |
| 52 | 80 | 800 |

The reactor was again cooled to 50° C and hydrogen pressure vented off. 300 grams of tetrahydrofuran and 2125 grams of toluene was then pressured into the reactor. The reactor was then discharged and the product solution filtered yielding 11425 grams of solution. The solution was analyzed and found to contain 26.8 wt. percent $NaAlEt_2H_2$ in a yield of 98 percent based on sodium, 100 percent based on triethyl aluminum.

EXAMPLE VI

Example V was repeated feeding 5950 grams of toluene, 300 grams of aluminum powder, 675 grams of sodium, and 240 grams of the 25 percent toluene solution of sodium aluminum diethyl dihydride. (60 grams of contained sodium aluminum diethyl dihydride, 8.9 percent on the sodium fed for the reaction with hydrogen). The time for the first reaction was 42 minutes.

| Time (Minutes) | Pressure (psig) Δ | Pressure (psig) Σ |
|---|---|---|
| 0 | — | — |
| 5 | 130 | 130 |
| 9 | 130 | 260 |
| 12 | 120 | 380 |
| 18 | 110 | 490 |
| 27 | 40 | 530 |
| 42 | 30 | 560 |

The amount of triethyl aluminum fed was 2330 grams. The time for the subsequent or second reaction with hydrogen was 71 minutes.

| Time (Minutes) | Pressure (psig) Δ | Pressure (psig) Σ |
|---|---|---|
| 0 | — | — |
| 1 | 140 | 140 |
| 3 | 110 | 250 |
| 8 | 150 | 400 |
| 15 | 120 | 520 |
| 23 | 90 | 610 |
| 36 | 60 | 670 |
| 50 | 80 | 750 |
| 65 | 60 | 810 |
| 71 | 10 | 820 |

EXAMPLE VII

A residual heel of several hundred milliliters retained from Example VI was used instead of feeding sodium aluminum diethyl dihydride. 670 grams of sodium, 300 grams of aluminum and 5000 grams of toluene were charged to the reactor. The reactor was heated to 220° C as in Example VI and then hydrogen fed for a 50 minute reaction at that temperature.

| Time (Minutes) | Pressure (psig) Δ | Pressure (psig) Σ |
|---|---|---|
| 0 | — | — |
| 4 | 17- | 170 |
| 9 | 141 | 310 |
| 18 | 100 | 410 |
| 29 | 40 | 450 |
| 38 | 20 | 470 |
| 50 | 10 | 480 |

Data from the Examples are plotted as follows.

| Example | FIG. |
|---|---|
| I | 1-A |
| II | 1-B |
| III | |
| IV | 1-C |
| V | 2-A |
| VI | 2-A |
| VII | 2-B |

Data for Example III follow the curve of FIG. 1-B.

I claim:
1. A process for producing alkali metal hydrides which comprises reacting alkali metal and hydrogen in the presence of a catalytic amount of at least about 0.001 percent by weight of alkali metal aluminum dihydrocarbon dihydride based on the alkali metal reactant fed to the process and in the presence of an inert solvent for the alkali metal aluminum dihydrocarbon dihy- dride, under conditions suitable to form alkali metal hydride, thereby producing alkali metal hydride.

2. The process of claim 1 wherein the alkali metal reacted is sodium, potassium or lithium.

3. The process of claim 1 wherein the alkali metal reacted with hydrogen and the alkali metal of the alkali metal aluminum dihydrocarbon dihydride are the same.

4. The process of claim 1 wherein the alkali metal aluminum dihydrocarbon dihydride used is of the formula $MAlR_2H_2$ wherein M is alkali metal and R is similar or different alkyl group having from about 2 to about 30 carbon atoms per alkyl group.

5. The process of claim 4 wherein R is similar or different alkyl group having from about 2 to about 6 carbon atoms per alkyl group.

6. The process of claim 1 wherein the alkali metal aluminum dihydrocarbon dihydride is sodium aluminum diethyl dihydride.

7. The process of claim 1 wherein the alkali metal aluminum dihydrocarbon dihydride is sodium aluminum diisobutyl dihydride.

8. The process of claim 1 wherein the temperature is from about 150° C to about 275° C.

9. The process of claim 1 wherein the temperature is from about 175° C to about 225° C.

10. The process of claim 1 wherein the catalytic quantity of alkali metal aluminum dihydrocarbon dihydride is from about 0.1 percent to about 50 percent by weight based on the alkali metal reactant fed to the process.

11. The process of claim 1 wherein the catalytic quantity of alkali metal aluminum dihydrocarbon dihydride is from about 1 percent to about 20 percent by weight based on the alkali metal fed to the process.

12. The process of claim 1 wherein the catalytic quantity of alkali metal aluminum dihydrocarbon dihydride is from about 10 to about 15 percent by weight based on the alkali metal fed to the process.

13. The process of claim 1 wherein the solvent is toluene, xylene or benzene.

14. The process of claim 1 for producing sodium hydride wherein the temperature is from about 150° C to about 275° C, wherein the pressure is from about 500 to about 1250 pounds per square inch gage, wherein the catalytic quantity of alkali metal aluminum dihydrocarbon dihydride is from about 10 to about 15 percent by weight based on the sodium fed to the process, and wherein the solvent is toluene.

15. The process of claim 1 for producing potassium hydride wherein potassium is reacted.

16. The process of claim 1 for producing lithium hydride wherein lithium is reacted.

17. The process of claim 1 wherein the solvent is toluene.

18. The process of claim 1 wherein the solvent is xylene.

19. The process of claim 1 wherein the solvent is benzene.

20. The process of claim 1 wherein the pressure is from about 50 to about 5000 pounds per square inch gage.

21. The process of claim 1 wherein the pressure is from about 500 to about 1250 pounds per square inch gage.

22. The process of claim 1 wherein the temperature is about 225° C.

23. The process of claim 1 wherein the alkali metal reacted is sodium and the product is sodium hydride.

24. The process of claim 1 wherein the temperature is from about 100° to about 325° C.

25. The process of claim 1 wherein the reaction time is from about 0.01 to about 12 hours.

* * * * *